(12) United States Patent
Borchert et al.

(10) Patent No.: US 7,217,679 B2
(45) Date of Patent: May 15, 2007

(54) CATALYTIC COATING FOR THE HYDROGENATION OF MALEIC ANHYDRIDE AND RELATED COMPOUNDS TO GIVE γ-BUTYROLACTONE, TETRAHYDROFURAN AND DERIVATIVES THEREOF

(75) Inventors: Holger Borchert, Offstein (DE); Stephan Schlitter, Limburgerhof (DE); Rolf-Hartmuth Fischer, Heidelberg (DE); Markus Rösch, Oppenheim (DE); Frank Stein, Bad Dürkheim (DE); Ralf-Thomas Rahn, Mannheim (DE); Alexander Weck, Freinsheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 259 days.

(21) Appl. No.: 10/433,008

(22) PCT Filed: Dec. 7, 2001

(86) PCT No.: PCT/EP01/14387

§ 371 (c)(1),
(2), (4) Date: May 29, 2003

(87) PCT Pub. No.: WO02/47815

PCT Pub. Date: Jun. 20, 2002

(65) Prior Publication Data

US 2004/0029728 A1    Feb. 12, 2004

(30) Foreign Application Priority Data

Dec. 11, 2000   (DE) ................ 100 61 555

(51) Int. Cl.
*B01J 37/02* (2006.01)
(52) U.S. Cl. .............. 502/304; 502/331; 502/345; 562/545

(58) Field of Classification Search ........ 502/304, 502/331, 345
See application file for complete search history.

(56) References Cited

U.S. PATENT DOCUMENTS

| | | |
|---|---|---|
| 3,065,243 A | 11/1962 | Dunlop et al. |
| 4,006,165 A | 2/1977 | Michalczyk et al. |
| 4,259,211 A * | 3/1981 | Krabetz et al. ........ 502/178 |
| 5,072,009 A | 12/1991 | Budge et al. |
| 5,122,495 A | 6/1992 | Taylor et al. |
| 5,149,836 A | 9/1992 | DeThomas et al. |
| 5,536,849 A | 7/1996 | Bergfeld et al. |
| 5,677,261 A | 10/1997 | Tenten et al. |
| 6,075,153 A | 6/2000 | Bergfeld et al. |

FOREIGN PATENT DOCUMENTS

| | | |
|---|---|---|
| DE | 196 23413 | 12/1997 |
| EP | 404 408 | 12/1990 |
| EP | 638 565 | 2/1995 |
| EP | 714 700 | 6/1996 |
| WO | 95/22539 | 8/1995 |
| WO | 97/24346 | 7/1997 |
| WO | 99/35139 | 7/1999 |
| WO | 99/38856 | 8/1999 |

* cited by examiner

*Primary Examiner*—Kamal A. Saeed
(74) *Attorney, Agent, or Firm*—Novak Druce & Quigg, LLP

(57) ABSTRACT

A catalyst for the hydrogenation of $C_4$-dicarboxylic acids and/or their derivatives, preferably maleic anhydride, in the gas phase comprises from 5 to 100% by weight, preferably from 40 to 90% by weight, of copper oxide and from 0 to 95% by weight, preferably from 10 to 60% by weight, of one or more metals or compounds thereof selected from the group consisting of Al, Si, Zn, Pd, La, Ce, the elements of groups III A to VIII A and groups I A and II A as active composition applied in the form of a thin layer to an inert support material.

21 Claims, No Drawings

US 7,217,679 B2

CATALYTIC COATING FOR THE HYDROGENATION OF MALEIC ANHYDRIDE AND RELATED COMPOUNDS TO GIVE γ-BUTYROLACTONE, TETRAHYDROFURAN AND DERIVATIVES THEREOF

The present invention relates to a process for preparing unsubstituted or alkyl-substituted γ-butyrolactone and tetrahydrofuran by catalytic hydrogenation in the gas phase of substrates selected from the group consisting of maleic acid and succinic acid and derivatives of these acids. For the purposes of the present invention, the latter are esters and anhydrides which, like the acids, may bear one or more alkyl substituents. The catalyst used is a coated catalyst comprising an inert support material and a thin layer comprising copper oxide and aluminum oxide applied thereto.

The preparation of γ-butyrolactone (GBL) and tetrahydrofuran (THF) by gas-phase hydrogenation of maleic anhydride (MA) is a reaction which has been known for many years. Numerous catalyst systems for carrying out this catalytic reaction are described in the literature. The majority of these are Cr-containing. Depending on the composition of the catalyst and the reaction parameters chosen, different product distributions are obtained using such catalysts.

Possible starting materials for preparing GBL and THF include not only MA but also maleic acid itself, succinic acid and its anhydride and also the esters of these acids. If GBL and THF bearing alkyl substituents are to be prepared, the appropriately alkyl-substituted species corresponding to the abovementioned acids, esters and anhydrides can be used.

U.S. Pat. No. 3,065,243 discloses a process in which copper chromite is use as catalyst. According to the description and examples, this reaction forms considerable amounts of succinic anhydride (SA) which has to be circulated. As is known, process engineering problems caused by crystallization of SA or succinic acid formed therefrom with subsequent blocking of pipes frequently occur.

Further copper chromite catalysts for the hydrogenation of MA are disclosed, for example, in U.S. Pat. Nos. 3,580, 930, 4,006,165, EP-A 638 565 and WO 99/38856. According to these disclosures, high yields of GBL can be achieved using the catalysts described there. THF is in each case formed only in traces. However, it is often the case that larger amounts of THF are desired for a number of reasons.

A process which allows this is disclosed in U.S. Pat. No. 5,072,009. The catalysts according to this patent have the formula $Cu_1Zn_bM_dO_x$ in which M is at least one element selected from the group consisting of the elements of groups IIA and IIIA, VA, VIII, Ag, Au, the elements of groups IIIB to VIIB of the Periodic Table of the Elements and the lanthanides and actinides; b is from 0.001 to 500, c is from 0.001 to 500 and d is from 0 to <200 and x corresponds to the number of oxygen atoms required according to valence criteria. Although it is stated that the catalysts corresponding to this patent do not have to contain any chromium, all examples describe chromium-containing catalysts. In these examples, a maximum THF yield of 96% is obtained, and the hydrogenation is carried out at pressures of from 20 to 40 bar.

A two-stage catalyst system for the hydrogenation of MA is described in U.S. Pat. No. 5,149,836. The catalyst for the first stage is chromium-free, and the catalyst for the second stage is based on Cu—Zn—Cr oxides.

An in-principle drawback of all the above-described catalyst systems is the presence of chromium oxide, whose use should be avoided owing to the acute toxicity. Such Cr-free catalyst systems for preparing GBL by hydrogenation of MA are also described in the prior art. Examples of such catalyst systems may be found in the publications WO 99/35139 (Cu—Zn oxide), WO 95/22539 (Cu—Zn—Zr) and U.S. Pat. No. 5,122,495 (Cu—Zn—Al oxide). All these catalyst systems make it possible to obtain high yields of GBL, up to 98%, but only traces of THF, if any, are formed. Although the formation of THF can, as is known, be favored by an increase in the reaction temperature or longer residence times in the reactor, this also increases the proportion of undesired by-products, for example butanol, butane, ethanol or ethane.

A catalyst made up of only copper oxide and aluminum oxide for the gas-phase hydrogenation of MA to GBL is disclosed in WO 97/24346. This too suffers from the same disadvantages as in the case of the publications described in the previous paragraph, namely only minor formation of THF which can be increased only by means of extreme reaction conditions.

The use of a catalyst having essentially the same composition as that described in WO 97/24346, namely based on Cu—Al oxides, is also described in JP 2 233 631. The object of that invention is to carry out the hydrogenation of MA in such a way that THF and 1,4-butanediol are formed as main products and only small amounts, if any, of GBL are formed. This is then achieved by the use of the catalysts based on mixed Cu—Al oxides and by adherence to particular reaction conditions. Typical mixtures obtained using this process comprise from about 15 to 20 mol % of 1,4-butanediol and from 60 to 80 mol % of THF; according to one example, the amount of THF can even be increased to above 99 mol %. This is achieved using a large excess of GBL as solvent. If, on the other hand, no solvent is employed, the yields drop considerably to values of about 75%.

All the catalysts disclosed in the abovementioned publications have a uniform structure. The components present are intimately mixed with one another, so that the structure is essentially homogeneous and the catalyst has no major constituents having a different composition.

In contrast, EP-A 0 404 408 discloses a catalyst for the hydrogenation of MA whose structure is in principle different from that of the catalysts in the abovementioned references. The catalytically active material corresponds essentially to the material disclosed in the above-cited U.S. Pat. No. 5,072,009. The material is then applied to an essentially inert, at least partly porous support having an external surface. The catalytically active material adheres to the external and internal surface area of the catalyst. In contrast to the corresponding catalyst which has not been applied to a support, which gives THF as main product, the supported catalyst preferentially forms GBL. Here too, Cr is present in all the catalysts in the examples. Another disadvantage is the large amount of SA formed.

All the types of catalyst described in the abovementioned publications have the disadvantage that they form a large amount of undesired by-product or can only be used for the preparation of one of the possible main products THF and GBL. The catalysts are frequently also Cr-containing.

It is an object of the present invention to provide a catalyst for the gas-phase hydrogenation of maleic acid and/or succinic acid and/or the abovementioned derivatives, which can be used variably for the preparation of unsubstituted or substituted THF and/or GBL. The catalyst should be free of Cr. In particular, this catalyst should make it possible to achieve high yields of THF with at the same time little formation of undesired by-products under appropriate reaction conditions.

We have found that this object is achieved by a catalyst for the hydrogenation of $C_4$-dicarboxylic acids and/or their derivatives in the gas phase, comprising from 5 to 100% by weight of copper oxide and from 0 to 95% by weight of one or more metals or compounds thereof selected from the group consisting of Al, Si, Zn, La, Ce, the elements of groups III A to VIII A and groups I A and II A as active composition applied in the form of a thin layer to an inert support material.

For the purposes of the present invention, the groups of the Periodic Table of the Elements are designated in accordance with the old IUPAC nomenclature.

For the purposes of the present invention, the term $C_4$-dicarboxylic acids and their derivatives refers to maleic acid and succinic acid which may be unsubstituted or have one or more $C_1$–$C_6$-alkyl substituents and also the anhydrides and esters of these unsubstituted or alkyl-substituted acids. An example of such an acid is citraconic acid. Preference is given to using MA.

The active composition of the catalyst of the present invention comprises copper oxide which is known per se and may optionally further comprise one or more additional metals selected from the abovementioned group or compounds thereof. The active composition preferably contains no Cr. The proportion of copper oxide ranges from 5 to 100% by weight, preferably from 40 to 90% by weight. The other metal or metals or their compounds are present in proportions of from 0 to 95% by weight, preferably from 10 to 60% by weight. It has been found that the activity of the catalyst increases in principle with increasing copper oxide content. The active composition of the catalyst preferably further comprises one or more metals from the group consisting of Al, Si, Zn, La, Ce, the elements of groups IIIA to VIIIA and the groups IA and IIA or compounds of these metals, with the compounds preferably being oxides. Preference is given to using, as a further metal, a metal from the group consisting of Al, Si, Ti, Zn, Zr, Pd, La and/or Ce or a compound thereof, preferably an oxide.

Pd, Zn, Zr and/or Al or their compounds are more preferred. In this preferred embodiment, the amount of copper oxide is in the range from 10 to 90%, in particular 40 to 90% by weight, and palladium, zinc, zirconium and/or aluminium oxide (s) are/is present in amounts of from 90 to 10% by weight, in particular 60 to 10% by weight. In case that one or more of the named metals or a compound thereof is/are present in addition to CuO, then Al or $Al_2O_3$ is preferred. In this case no or one further metal or a compound thereof is present. In case one further metal is present, this is preferably Pd or a compound thereof. The catalyst according to the present invention thus consists, besides the usual impurities optionally present, in particular of Cu and Al or oxides thereof or Cu, Al and Pd or oxides thereof, with both embodiments being of equal importance. The respective metals may be present in the mixed catalyst used according to the present invention in the form of a salt, preferably the oxide, or in elemental form. The latter is formed, in particular, under a reducing hydrogen atmosphere. In case the catalyst contains the aforementioned metals or compounds thereof, preferably no further components are present, besides the usual inpurities known to the person skilled in the art.

The active composition is prepared in a manner known per se, for example by precipitation of the corresponding metal carbonates and/or hydroxides in aqueous solution, washing, drying and calcination. The metal carbonates or hydroxides are obtainable by, for example, dissolving the corresponding metal salts in water and adding sodium carbonate solution. Metal salts used are, for example, nitrates, sulfates, chlorides, acetates or oxalates. The composition is then applied to the support in a customary manner, for example by mixing the pulverulent oxide mixture with the support in a stirred drum in the presence of a binder or adhesive. It is also possible to treat the support with precursors of the active composition, for example the abovementioned carbonates, nitrates, oxalates or hydroxides of the respective metals. In this method, the respective metal compounds can be mixed and applied in one step or else can be applied in succession. This pretreated support is then subjected to heat treatment to produce the active composition.

Finally, it is also possible to produce the catalyst by suspending the pulverulent active composition and the support in water or an organic liquid and removing the water or the organic liquid until the catalyst is dry, for example by means of heating.

The amount of active composition as a proportion of the total mass of the catalyst is from 5 to 60% by weight, preferably from 15 to 30% by weight. If these values are exceeded, the resulting behavior approximates that of an all-active catalyst having the same composition of active material. On the other hand, if the content of active composition is too low, an unsatisfactorily low activity per unit volume of catalyst is found.

Materials which are suitable for producing the support are nonporous support materials known per se. The support should have a surface area of <0.5 $m^2$/g and a porosity of <0.05 $cm^3$/g. Compared to porous supports used, for example, in accordance with EP-A 404 408, these give a higher mechanical stability and a higher bulk density of the catalyst. In addition, there is no limit above which the support can no longer take up active composition because the entire pore volume is occupied. Examples of suitable support materials include aluminum oxide, sintered alumina ($\alpha$-$Al_2O_3$ ignited at high temperature), aluminum silicates such as mullite, magnesium silicates such as steatite, magnesium-aluminum silicates such as cordierite, glass, silicon carbide, silicon dioxide, steel and other ceramic materials known to those skilled in the art. The support is inert. A rough surface of the support material may aid adhesion of the active composition. The support material is preferably selected from the group consisting of steatite, mullite, cordierite, silicon carbide and aluminum oxide ignited at high temperature. In particular, the support material is steatite.

Before being coated, the support material is converted into shaped bodies serving as supports. The geometry of this inert shaped body and thus the resulting coated catalyst of the present invention is not critical. Suitable geometries are, for example, spheres, saddles, solid cylinders and hollow cylinders.

Owing to the use of nonporous supports and the production process of the present invention, the catalysts of the present invention have a specific structure. Here, the active composition is present in the form of a thin, coherent layer on the outer surface of the support. Due to the lack of pores and the coating process selected, no active composition is present in the support itself.

Suitable reactors for the reaction are reactors in which the catalyst is present as a fixed bed. Particular preference is given to shell-and-tube reactors so that the heat liberated in the reaction can be readily removed. MA is vaporized and passed through the reactor together with a hydrogen-containing gas stream. Preference is given to a mixture having a high hydrogen content. In some cases, the introduction of other gaseous components such as water vapor, hydrocarbons, e.g. methane, ethane or n-butane, or carbon monoxide has a favorable effect on the selectivity, activity or long-term stability.

The concentration of MA is from 0.1 to 5% volume, preferably from 0.2 to 2% by volume. At significantly higher MA concentrations, MA condenses in the reactor and coats the catalyst with a liquid film. Concentrations which are significantly lower than those indicated above are possible in principle, but these would reduce the space-time yield and make the process unnecessarily expensive. The temperature of the reaction is set to values in the range from 150 to 400° C., preferably from 200 to 300° C. Higher temperatures favor the formation of by-products, while lower temperatures lead to an unnecessary loss in activity of the catalyst.

The pressure is set to values in the range from 0.5 to 50 bar, preferably from 1 to 10 bar. The GHSV (gas hourly space velocity=volume flow of the reaction gas at STP divided by the catalyst bed volume) is set so that complete MA conversion is achieved. This makes the work-up of the product mixture easier and saves recirculation of unreacted MA. The GHSV is from 10 to 50 000 $h^{-1}$, preferably from 100 to 10,000 $h^{-1}$. Variation of the GHSV makes it possible to control the product distribution. The product mixture can be separated by methods known to those skilled in the art. At least part of the unreacted hydrogen is preferably circulated and thus reused in the hydrogenation.

In general, the catalyst is subjected to activation, usually a pretreatment with hydrogen, before use in the reaction. This produces the active catalyst species by partial reduction of the oxides present in the catalyst mixture to the elemental metal which is active in the catalytic reaction carried out according to the present invention.

It has been found that the formation of the desired end products can be controlled by varying the reaction parameters. These are, in particular, pressure, temperature and GHSV. Thus, an increased, sometimes exclusive, formation of THF is generally found at high pressure and temperature and low GHSV values. On the other hand, low pressures and temperatures and high GHSV values lead to increased formation of GBL.

The catalyst of the present invention has a satisfactory operating life. However, should the activity and/or selectivity of the catalyst drop during operation, it can be regenerated by means of measures known to those skilled in the art. These include reductive treatment of the catalyst in a stream of hydrogen at elevated temperature. The reductive treatment can, if necessary, be preceded by an oxidative treatment. In this case, a gas mixture comprising molecular oxygen, for example air, is passed at elevated temperature through the catalyst bed. It is also possible to wash the catalyst with a suitable solvent, for example methanol, THF or GBL, and subsequently to dry it by means of a gas stream.

The invention is illustrated by the following examples.

EXAMPLE 1

Production of a Coated Catalyst According to the Present Invention a) Preparation of the Active Composition 1.5 l of water are placed in a heatable precipitation vessel fitted with a stirrer and are heated to 80° C. Over a period of one hour, a metal salt solution comprising 877 g of $Cu(NO_3)_2*2.5H_2O$ and 1472 g of $Al(NO_3)_3*9H_2O$ in 2000 ml of water and at the same time a 20% strength by weight sodium carbonate solution are metered into this precipitation vessel while stirring. The rate of introduction of sodium carbonate is selected so that a pH of 6 is established in the precipitation vessel. After all the metal salt solution has been added, further sodium carbonate solution is metered in until the pH in the precipitation vessel has reached a value of 8, and the mixture is stirred for another 15 minutes at this pH. The total consumption of sodium carbonate solution is 5.5 kg. The suspension formed is filtered and the solid is washed with water until the washings no longer contain any nitrate (<25 ppm). The filter cake is firstly dried at 120° C. and subsequently calcined at 600° C.

b) Production of the Coated Catalyst 500 ml of surface-roughened steatite spheres having a diameter of 4–5 mm (from Chemtech) are placed in an impregnation drum and sprayed with 10 ml of water/glycerol mixture (3:1). 170 g of the active composition milled to a particle size of <100 µm and a further 140 ml of the water/glycerol mixture are then added continuously, so that the support is homogeneously coated with powder. The coated support is dried firstly at 120° C. for 2 hours and then at 300° C. for 2 hours while circulating air over it.

EXAMPLE 2

Production of a Coated Catalyst According to the Present Invention 500 ml of surface-roughened steatite spheres having a diameter of 2–3 mm (from Chemtech) are placed in an impregnation drum and sprayed with 15 ml of water/glycerol mixture (3:1). 163 g of the active composition from Example 1 milled to a particle size of <100 µm and a further 150 ml of the water/glycerol mixture are then added continuously, so that the support is homogeneously coated with powder. The coated support is dried firstly at 120° C. for 2 hours and then at 300° C. for 2 hours while circulating air over it.

EXAMPLE 3

Production of a Coated Catalyst According to the Present Invention 500 ml of surface-roughened steatite spheres having a diameter of 2–3 mm (from Chemtech) are placed in an impregnation drum and sprayed with 15 ml of water/glycerol mixture (3:1). 433 g of the active composition from Example 1 milled to a particle size of <100 µm and a further 370 ml of the water/glycerol mixture are then added continuously, so that the support is homogeneously coated with powder. The coated support is dried firstly at 120° C. for 2 hours and then at 300° C. for 2 hours while circulating air over it.

EXAMPLE 4

Production of a Coated Catalyst According to the Present Invention a) Preparation of the Active Composition To 220 g of the active composition of example 1 a) are added, with stirring, 273 ml of an aqueous solution of palladium nitrate (noble metal contents: 2.2 g Pd), followed by intimate mixing. The humid product is dried at 100° C. and then calcinated at 350° C.

b) Production of Coated Catalyst of the Present Invention 500 ml of surface-roughened steatite spheres having a diameter of 4–5 mm (from Chemtech) are placed in an impregnation drum and sprayed with 12 ml of water/glycerol mixture (3:1). 170 g of the active composition from Example 4a milled to a particle size of <100 µm and a further 140 ml of the water/glycerol mixture are then added continuously, so that the support is homogeneously coated with powder. The coated support is dried firstly at 120° C. for 2 hours and then at 300° C. for 2 hours while circulating air over it.

EXAMPLE 5

Production of a Coated Catalyst According to the Present Invention a) Preparation of the Active Composition To 100 g of the active composition of example 1 a) are added, with stirring, 124 ml of an aqueous solution of palladium nitrate (noble metal contents: 11.1 g Pd), followed by intimate mixing. The humid product is dried at 100° C. and then calcinated at 450° C.

b) Production of the Coated Catalyst of the Present Invention 500 ml of surface-roughened steatite spheres having a diameter of 45 mm (from Chemtech) are placed in an impregnation drum and sprayed with 15 ml of water/glycerol mixture (3:1). 153 g of the active composition from Example 1a milled to a particle size of <100 µm and a further 135 ml of the water/glycerol mixture are then added continuously, so that the support is homogeneously coated with powder. Thereafter the coating procedure is continued with 17 g of the active composition from example 5a) milled to a particle size of <100 µm and a further 15 ml of the water/glycerol mixture. The coated support is dried firstly at 120° C. for 2 hours and then at 300° C. for 2 hours while circulating air over it.

EXAMPLE 6

Production of a Coated Catalyst According to the Present Invention a) Preparation of the Active Composition 2.7 l of water and 224 g of boehmite (Pural SB, from Condea. $Al_2O_3$ content=about 72%) are placed in a heatable precipitation vessel fitted with a stirrer and are heated to 50° C. Over a period of half an hour, 2500 ml of a metal salt solution comprising 993 g of $Cu(NO_3)_2*3H_2O$ and 1187 g of $Zn(NO_3)_3*6H_2O$ and at the same time a 20% strength by weight sodium carbonate solution are metered into this precipitation vessel while stirring. The rate of introduction of sodium carbonate is selected so that a pH of 6.2 is established in the precipitation vessel. The consumption of sodium carbonate solution is 4.6 kg. The suspension formed is filtered and the solid is washed with water until the washings no longer contain any nitrate (<25 ppm). The filter cake is firstly dried at 120° C. and subsequently calcined at 300° C.

b) Production of the Coated Catalyst of the Present Invention 500 ml of surface-roughened steatite spheres having a diameter of 4–5 mm (from Chemtech) are placed in an impregnation drum and sprayed with 10 ml of water/glycerol mixture (3:1). 170 g of the active composition from Example 6a milled to a particle size of <200 µm and a further 125 ml of the water/glycerol mixture are then added continuously, so that the support is homogeneously coated with powder. The coated support is dried firstly at 120° C. for 2 hours and then at 300° C. for 2 hours while circulating air over it.

EXAMPLE 7

Production n of a Coated Catalyst According to the Present Invention a) Preparation of the Active Composition The preparation of Example 6a is repeated, but the material is calcined at 800° C.

b) Production of the Coated Catalyst 500 ml of surface-roughened steatite spheres having a diameter of 45 mm (from Chemtech) are placed in an impregnation drum and sprayed with 10 µml of water/glycerol mixture (3:1), 70 g of the active composition from Example 7a milled to a particle size of <200 µm and a further 50 ml of the water/glycerol mixture are then added continuously, so that the support is homogeneously coated with powder. The coated support is dried firstly at 120° C. for 2 hours and then at 300° C. for 2 hours while circulating air over it.

EXAMPLE 8

Production of a Coated Catalyst According to the Present Invention 500 ml of surface-roughened steatite spheres having a diameter of 45 mm (from Chemtech) are placed in an impregnation drum and sprayed with 10 ml of water/glycerol mixture (3:1). 285 g of the active composition from Example 7a milled to a particle size of <200 µm and a further 70 ml of the water/glycerol mixture are then added continuously, so that the support is homogeneously coated with powder. The coated support is dried firstly at 120° C. for 2 hours and then at 300° C. for 2 hours while circulating air over it.

EXAMPLE 9

Hydrogenation of Maleic Anhydride 200 ml of the catalyst from Example 1 (total mass=216.1 g) are placed in a tube reactor. The reactor is heated and the reaction gas flows through it from the top downward. MA is pumped as a melt into a vaporizer operated at 200° C. where it is vaporized in a stream of hydrogen and it is then passed through the reactor. The pressure in the reactor was 5 bar. The GHSV was set so that complete conversion of MA was achieved by varying the volume flow through the reactor. The results are shown in Table 1.

Before the MA/hydrogen mixture was fed into the reactor, the catalyst was subjected to a pretreatment with hydrogen. For this purpose, the reactor was firstly flushed with 200 standard l/h of nitrogen at atmospheric pressure and at the same time heated over a period of one hour to a temperature in the catalyst bed of 180° C. The volume flow of nitrogen was then increased to 950 standard l/h and 50 standard l/h of hydrogen were additionally fed in. This resulted in a slight temperature increase in she catalyst bed to about 250° C. After the temperature in the entire catalyst bed had dropped to 190° C., the volume flow of nitrogen was gradually decreased to 500 standard l/h and the flow of hydrogen was increased to 500 standard l/h. The nitrogen flow was finally turned off and the flow of hydrogen was increased to 600 standard l/h.

EXAMPLE 10

Hydrogenation of Maleic Anhydride

Example 9 was repeated using 200 ml of the catalyst from Example 2. The results are shown in Table 1.

EXAMPLE 11

Hydrogenation of Maleic Anhydride

Example 9 was repeated using 200 ml of the catalyst from Example 3. The results are shown in Table 1.

EXAMPLE 12

Hydrogenation of Maleic Anhydride

Example 9 was replated using 200 ml of the catalyst from Example 4. The results of the catalytic tests are given in Table 1.

EXAMPLE 13

Hydrogenation of Maleic Anhydride

Example 9 was replated using 200 ml of the catalyst from Example 5. The results of the catalytic tests are given in Table 1.

EXAMPLE 14

Hydrogenation of Maleic Anhydride

Example 9 was repeated using 200 ml of the catalyst from Example 6. The results are shown in Table 1.

EXAMPLE 15

Hydrogenation of Maleic Anhydride

Example 9 was repeated using 200 ml of the catalyst from Example 7. The results are shown in Table 1.

EXAMPLE 16

Hydrogenation of Maleic Anhydride

Example 9 was repeated using 200 ml of the catalyst from Example 8. The results are shown in Table 1.

COMPARATIVE EXAMPLE 1

Production of a Comparative Catalyst 400 g of the active composition from Example 1 are comminuted to a particle size of <1 mm, admixed with 3% by weight of graphite powder, intimately mixed and pressed to form pellets having a diameter of 3 mm and a height of 3 mm.

COMPARATIVE EXAMPLE 2

Example 9 was repeated using 100 ml of the all-active catalyst from Comparative Example 1. The results of the catalytic tests are given in Table 1.

It can be seen from Table 1 that the coated catalyst gives a higher THF selectivity than the all-active catalyst comprising the same active composition (experiments 9.1 and 1x) at comparable temperature and MA inlet concentration. The activity of the coated catalyst per unit volume of the bed is somewhat lower, and a higher GHSV can be set in the case of the all-active catalyst. By doping the coated catalyst with palladium, the activity level of non doped all-active catalysts can be reached. Also in the case of non-doping, the advantage of higher selectivity outweighs the lower activity level, since the additional costs for catalyst and a larger reactor constitute a negligible proportion of the total process costs. On the other hand, the coated catalyst gives high GBL yields when the GHSV is increased only slightly, without large amounts of SA being formed at the same time (experiment 9.3). The THF selectivity of the all-active catalyst cannot be increased above 80% even when the temperature, the GHSV or the MA concentration is varied (experiments 1x, 2x, 3x). The coated catalyst therefore makes it possible to obtain a significantly more flexible THF/GBL product mix than does the all-active catalyst. The latter gives a significantly lower GBL yield with at the same time increased SA formation (experiment 4x).

We claim:

1. A coated chromium-free catalyst for the hydrogenation of $C_4$-dicarboxylic acids and/or their derivatives in the gas phase, comprising from 5 to 100% by weight of copper oxide and an amount up to 95% by weight of one or more metals or compounds thereof selected from the group consisting of Al, Si, Ti, Zn, Zr, Pd, La and Ce and compounds thereof as active composition applied in the form of a thin layer to an inert support material, wherein the support material has a surface area of <0.5 $m^2/g$ and a porosity of <0.05 $cm^3/g$.

2. A catalyst according to claim 1, wherein the said derivative is malice anhydride.

3. A catalyst according to claim 1 comprising, 40 to 90% by weight of copper oxide and 10 to 60% by weight of the one or more metals or compounds thereof.

4. A catalyst according to claim 1, wherein the compound of the one or more metals is an oxide.

TABLE 1

| Example | Catalyst | Experiment | GHSV [$h^{-1}$] | T [° C.] | $C°_{MA}$ [% by volume] | $S_{SA}$ [mol %] | $S_{GBL}$ [mol %] | $S_{THF}$ [mol %] | $S_{by\text{-}prod.}$ [mol %] |
|---|---|---|---|---|---|---|---|---|---|
| 9 | Coated catalyst from Example 1 | 9.1 | 1000 | 270 | 1.2 | 0 | 0 | 95.9 | 4.1 |
|  |  | 9.2 | 1000 | 257 | 0.7 | 0 | 0 | 96.3 | 3.7 |
|  |  | 9.3 | 1500 | 270 | 1.1 | 11.1 | 85.2 | 3.7 | 0 |
| 10 | Coated catalyst from Example 2 | 10.1 | 1000 | 270 | 1.2 | 0 | 0 | 94.8 | 6.2 |
|  |  | 10.2 | 1250 | 268 | 1.1 | 10.2 | 80.7 | 8.3 | 0.7 |
| 11 | Coated catalyst from Example 3 | 11.1 | 1000 | 270 | 1.2 | 0 | 0 | 92.7 | 7.3 |
|  |  | 11.2 | 3000 | 270 | 2.0 | 0 | 37.6 | 55.1 | 7.3 |
| 12 | Coated catalyst from Example 4 | 12.1 | 2000 | 250 | 1.2 | 0 | 0 | 95.0 | 5.0 |
| 13 | Coated catalyst from Example 5 | 13.1 | 2000 | 245 | 1.2 | 0 | 4.6 | 91.5 | 3.9 |
| 14 | Coated catalyst from Example 6 | 14.1 | 1000 | 270 | 1.2 | 0.3 | 89.7 | 8.3 | 1.7 |
| 15 | Coated catalyst from Example 7 | 15.1 | 1000 | 270 | 1.2 | 0.1 | 0.5 | 95.4 | 4.0 |
|  |  | 15.2 | 1000 | 260 | 1.0 | 7.4 | 84.9 | 7.7 | 0 |
| 16 | Coated catalyst from Example 8 | 16.1 | 1000 | 270 | 1.4 | 3.5 | 88.7 | 7.8 | 0 |
|  |  | 16.2 | 1000 | 270 | 1.2 | 0.2 | 0 | 95.9 | 3.9 |
| Comparative Example 2 | All-active catalyst from Comparative Example 1 | 1x | 2500 | 270 | 1.0 | 0.1 | 0.5 | 88.9 | 10.5 |
|  |  | 2x | 5400 | 230 | 0.2 | 0 | 2.3 | 86.9 | 10.2 |
|  |  | 3x | 5100 | 290 | 1.0 | 0 | 0.2 | 84.5 | 14.3 |
|  |  | 4x | 6000 | 250 | 1.1 | 42.3 | 51.9 | 5.4 | 0.4 |

$C°_{MA}$ = inlet concentration of MA
$S_{XXX}$ = selectivity of the respective product

5. A catalyst as claimed in claim 1, wherein the further metal or metals are selected from the group consisting of Pd, Zn, Zr and Al and oxides thereof, with this/these being present in an amount of from 10 to 90% by weight, and the copper oxide being present in an amount of from 90 to 10% by weight.

6. A catalyst as claimed in claim 5, wherein the further metal or the oxide thereof is present in an amount of from 10 to 60% by weight and the copper oxide is present in an amount of from 90 to 10% by weight.

7. A catalyst according to claim 5, wherein the catalyst comprises CuO and $Al_2O_3$ and optionally Pd or a compound thereof as a further component, or consists of the said components.

8. A catalyst as claimed in claim 1, wherein the support material is selected from the group consisting of aluminum oxide, sintered alumina, aluminum silicates, magnesium silicates, magnesium-aluminum silicates, glass, silicon carbide, silicon dioxide and steel.

9. A catalyst as claimed in claim 8, wherein the support material is selected from steatite, mullite, cordierite, silicon carbide and sintered alumina.

10. A catalyst as claimed in claim 8, wherein the support material is steatite.

11. A catalyst as claimed in claim 1, whose active composition makes up from 5 to 60% by weight, of the total mass of the catalyst.

12. A catalyst as claimed in claim 11, whose active composition makes up from 15 to 30% by weight of the total mass of the catalyst.

13. A process for hydrogenating $C_4$-dicarboxylic acids and/or their derivatives, in the gas phase in the presence of a catalyst as claimed in claim 1.

14. A process as claimed in claim 13 which is carried out at a GHSV of from 20 to $50000h^{-1}$.

15. A process as claimed in claim 14, wherein the GHSV is from 100 to $10,000h^{-1}$.

16. A process as claimed in claim 13, wherein the reaction temperature is from 150 to 400° C., and the pressure during the reaction is from 0.5 to 50 bar.

17. A process as claimed in claim 16, wherein the reaction temperature is from 200 to 300° C.

18. A process as claimed in claim 16, wherein the pressure is from 1 to 10 bar.

19. A process as claimed in claim 13, wherein the concentration of $C_4$-dicarboxylic acid or its derivative is from 0.5 to 5% by volume.

20. A process as claimed in claim 13, wherein the concentration is from 0.2 to 2% by volume.

21. A process for producing a catalyst as claimed in claim 10, which comprises preparing the desired active composition and applying it by methods known per se to a suitable support or applying precursor compounds of the appropriate active composition by methods known per se to the support material and converting the precursor compounds into the active composition.

\* \* \* \* \*